United States Patent [19]

Bouwman et al.

[11] Patent Number: 4,551,306
[45] Date of Patent: Nov. 5, 1985

[54] SEALED REAGENT MATRIX

[75] Inventors: Dale W. Bouwman; Harold K. Clayborn, both of Elkhart, Ind.

[73] Assignee: Miles Laboratories, Inc., Elkhart, Ind.

[21] Appl. No.: 496,452

[22] Filed: May 20, 1983

[51] Int. Cl.[4] ............................................. G01N 33/52
[52] U.S. Cl. ........................................ 422/56; 422/57
[58] Field of Search ........................... 422/56, 57, 58; 435/805, 28; 436/95

[56] References Cited

U.S. PATENT DOCUMENTS

| | | | |
|---|---|---|---|
| 3,001,915 | 9/1961 | Fonner | 422/56 |
| 3,006,735 | 10/1961 | Jordan | 422/56 X |
| 3,232,710 | 2/1966 | Rieckmann et al. | 422/57 X |
| 3,443,903 | 5/1969 | Haack et al. | 422/56 X |
| 3,715,192 | 2/1973 | Wenz et al. | 422/56 |
| 4,160,008 | 7/1979 | Fenocketti et al. | 422/56 |
| 4,301,115 | 11/1981 | Rapkin et al. | 422/57 X |

*Primary Examiner*—Arnold Turk
*Attorney, Agent, or Firm*—Roger N. Coe

[57] ABSTRACT

Edges of reagent matrix are sealed such that liquid present in the reagent matrix material is retained therein and prevented from running over into another reagent matrix area present on the same reagent test device.

7 Claims, No Drawings

SEALED REAGENT MATRIX

BACKGROUND OF THE INVENTION

1. Field of the Invention

The present invention relates to sealed reagent matrix and, more particularly, to reagent matrix material which has had a sealing composition applied to its edges to prevent or minimize cross-contamination of reagents during use.

The art of analytical chemistry has been greatly advanced since biochemistry began emerging as a primary scientific frontier, requiring increasingly sophisticated analytical methods and tools to solve problems. Likewise the medical profession has lent impetus to the growth of analytical chemistry, with its desiderata of both high precision and speed in obtaining results.

To satisfy the needs of the medical profession as well as other expanding technologies, such as the brewing industry, chemical manufacturing, etc., a myriad of analytical procedures, compositions and apparatus have evolved, including the so-called "dip-and-read" type reagent test device. Reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a reagent strip test device into a sample of body fluid, such as urine or blood, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular constituent in a test sample, but also an estimate of how much of the constituent is present. Such test devices provide the physician with a facile diagnostic tool as well as the ability to gage the extent of disease or of bodily malfunction.

Illustrative of such test devices currently in use are products available from the Ames Division of Miles Laboratories, Inc. under the trademarks CLINISTIX, MULTISTIX, KETOSTIX, N-MULTISTIX, DIASTIX, DEXTROSTIX, and others. Test devices such as these usually comprise one or more carrier matrices, such as absorbent paper, having incorporated therein a particular reagent or reactant system which manifests a detectable response, e.g., a color change, in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the test device with a sample is indicative of the presence of a particular constituent and/or its concentration in the sample. Some of these test devices and their reagent systems are set forth in U.S. Pat. Nos. 3,123,443; 3,212,855; 3,814,668; etc.

Thus, it is customary for reagent test devices to contain more than one reagent bearing carrier matrix, in which each reagent bearing carrier matrix is capable of detecting a particular constituent in a liquid sample. For example, a reagent test device could contain a reagent bearing carrier matrix responsive to glucose in urine and another matrix responsive to ketones, such as acetoacetate, which is spaced from, but adjacent to, the glucose responsive matrix. Such a product is marketed by the Ames Division of Miles Laboratories, Inc. under the trademark KETO-DIASTIX. Another reagent test device marketed by the Ames Division of Miles Laboratories, Inc., N-MULTISTIX, contains eight adjacent reagent incorporated matrices providing analytical measurement of pH, protein, glucose, ketones, bilirubin, occult blood, nitrite, and urobilinogen.

Despite the obvious, time-proven advantages of such multiple reagent test devices as these, misuse can result in misinformation. These multiple analysis tools comprise complex chemical and catalytic systems, each reagent matrix containing a unique reactive system, responsive to its particular analyte. Thus, it is possible, if the reagent test device is misused, for chemicals to be transported by the liquid sample being analyzed from one carrier matrix on the reagent test device to another. Should this happen it is possible for reagents from one carrier matrix to interfer with those of the other so contacted causing unreliable results. Although it is common in the reagent test device industry to provide detailed instructions of how this problem is avoided, i.e., directions for properly manipulating the reagent test devices by blotting excess fluid, etc., nevertheless ignorance or disregard of these instructions could permit reagents from one matrix to run over onto an adjacent one. It is the prevention of this "runover" problem that the present invention is primarily directed.

The elimination of runover has been long sought after and the present discovery, which is the cumulation of an extensive research effort, provides a very effective solution to this problem.

2. Discussion of the Prior Art

The patent literature is replete with accounts of myriad attempts at curtailing runover, the great bulk of the emphasis being directed to two basic concepts: the adsorbance of runover liquid by bibulous layers placed beneath the reagent-bearing layers of reagent test devices; and the use of hydrophobic barriers between the spaced matrices. The former has met with moderate success, whereas the latter approach has not.

Of the multilayer type reagent test devices, U.S. Pat. No. 4,160,008 describes a test device in which the carrier matrices containing reagent formulations are provided with adsorbent underlayers which are separated therefrom by sample impervious barrier layers. Each matrix thus forms the upper layer of a laminate composite in which the barrier layer is disposed between the matrix and the adsorbent base layer, the composite being fixed to a suitable support such as a plastic substrate. When the test device is dipped into the liquid sample the portion of sample which would otherwise runover from one matrix to another is largely adsorbed into the underlayer of the latter through the exposed sides, the barrier layer of the composite segregating the adsorbed runover from the upper reagent layer.

U.S. Pat. No. 4,301,115 discloses and claims a test device comprising a base support member coated with a hydrophobic barrier layer to which a plurality of spaced apart reagent matrices are affixed. This approach virtually eliminates cross-contamination between adjacent reagent areas of multiple reagent test devices, but requires an extra step of applying hydrophobic material to the base support member of the reagent test device.

With respect to the development and use of barriers and/or barrier materials between reagent matrices, the patent art is replete with teachings, which in theory, at least, would seem to overcome the runover problem.

U.S. Pat. No. 3,418,083 discloses an indicator-impregnated adsorbent carrier matrix treated with wax, oil or similar "hydrophobic" agents. It is stated that when a sample of blood is placed on the resulting reagent test device, only colorless liquid components permeate it, the proteinaceous, colored blood components remain on the surface where they can be removed. Thus, it is taught that the liquid portion bearing the analysate permeates the reagent matrix pad and color interference is precluded.

Still another prior art patent U.S. Pat. No. 3,001,915, describes an adsorbent paper reagent test device having spaced reagent-impregnated test areas for more than one sample component, each such area being separated from the other reagent-impregnated test area by a nonadsorbent barrier portion. The barrier is provided by impregnation of the paper strip with materials such as polystyrene, rosin, paraffin and various cellulose esters. The reagent strip is prepared, according to the reference, by impregnating a portion of the paper strip with a glucose sensitive reagent system. When dry, a solution of one or more of the barrier materials is applied to the paper adjacent a glucose sensitive portion. After further drying a protein sensitive reagent system is applied and the process is repeated with alternate applications of reagent and barrier solutions with drying steps inbetween.

Yet an earlier patent, U.S. Pat. No. 2,129,754, describes the impregnation of filter paper with paraffin wax whereby specific areas are left unimpregnated and these areas are treated with indicator systems for a particular analyte.

In U.S. Pat. No. 3,006,735 the concept of barrier material impregnated between reagent areas of a reagent test device is carried one step further by providing successive reagent areas responsive to different degrees of water hardness. Water repellent material, such as oils, waxes, silicones, and printer's varnish, is impregnated between these reagent test areas. Like the proceeding two patents this citation is restricted to paper or like bibulous material wherein reagent and barrier material alike are impregnated sequentially along its length.

Similarly U.S. Pat. Nos. 3,011,874 and 3,127,281 teach the use of hydrophobic barrier materials impregnated in part of a reagent test device in order to separate one reagent area from another and thereby avoid contamination.

Yet another patent which mentions the separation of indicator reagent sites by the use of nonadsorbent or hydrophobic materials is U.S. Pat. No. 3,964,871.

Whereas the foregoing patents represent what is believed to be the most pertinent prior art to the present invention, it should be noted that currently marketed reagent test device products for the most part contain reagent impregnated matrices affixed to hydrophobic organoplastic material. Thus, the multiple reagent test device known as N-MULTISTIX contains eight different reagent impregnated matrices mounted on a polystyrene film. Since polystyrene is hydrophobic, the reagent strip can be said to have hydrophobic interstices between adjacent matrices.

Despite lip service given by prior art accounts of eliminating runover, the fact remains that the problem continues to exist. The approaches disclosed in U.S. Pat. Nos. 4,160,008 and 4,301,115 have come the closest to eliminating this runover problem.

Prior art attempts using wax, oils, silicones, etc., have not curtailed runover to a clinically significant extent; and what modest advances have been made are more than offset by serious drawbacks inherent to such attempts. For example, applying hydrophobic material only at reagent area interstices embodies enormous technical problems, especially when compared with the current technics for manufacturing dip-and-read reagent test devices. Besides the obvious extra steps required by interstitial application, there is the danger of some of the hydrophobic material overlapping the reagent area thereby interfering with the paramount purpose of the reagent test device. Moreover, none of the prior art substances provides a suitable surface for adhesion.

Even if the above shortcomings were not prohibitive enough, the prior art hydrophobic substances lack a degree of hydrophobicity required to prevent runover. They do not provide a sufficient contact angle to achieve the required hydrophobicity, nor do they provide a suitable surface for binding either the adsorbent matrices or the reagent themselves, where they are coated directly on the substrate surface.

The present invention virtually eliminates cross-contamination between adjacent reagent areas of multiple reagent test device matrices. The results are truly incontrovertible and the success achieved in solving this problem compares favorably with the use of a hydrophobic barrier layer, as described in U.S. Pat. No. 4,301,115. Moreover, the present invention does not require the presence of an additional layer applied to the substrate of reagent test devices. The present invention, involving the sealing of two of the edges of a reagent matrix area, can be accomplished quickly and inexpensively during conventional procedures used for forming reagent test devices.

SUMMARY OF THE INVENTION

An object of the present invention is to seal the edges of reagent matrix material and hence carrier matrices in a way which prevents or substantially eliminates runover problems on reagent test devices containing multiple carrier matrices.

Another object of the present invention is to substantially eliminate runover problem by sealing the edges of reagent matrix material during the production of the reagent test devices in a manner which does not interfer with the impregnated reagents in the carrier matrix.

Still another object of the present invention is to provide an inexpensive and effective means of eliminating or materially reducing runover.

In accordance with the present invention, two opposite sides of a reagent matrix material are sealed prior to the application of the reagent matrix material to a substrate material by means of double backed adhesive material and then slitting the resulting reagent cards to provide individual reagent test devices. The sealing process can be accomplished as described in copending Ser. No., 496,453, now U.S. Pat. No. 4,482,583 filed concurrently herewith, employing a v-groove applicator roll which picks up sealing material, such as paraffin, from a heated container and applies it to the edges of reagent ribbon such that only the edges of the reagent ribbon are sealed and the sealing material never contacts the reagent matrix ribbon except at its peripheral edges. A wide variety of sealing materials can be used, including materials which have been recognized in the past as effective water repellent materials.

DESCRIPTION OF THE PREFERRED EMBODIMENTS

In accordance with the present invention, reagent matrix material is sealed with sealing material, such as liquid paraffin applied to two edges of the matrix material. By applying sealing liquid material only to edges of the reagent matrix, the reagent in the impregnated matrix is not affected. Accordingly, upon drying, the sealing liquid effectively seals opposite ends or edges of the reagent matrix material and does not interfer with the reaction which takes place when the reagent test device is dipped into a liquid, such as a body fluid or industrial liquid, to be tested.

The sealing material utilized to seal the edges of the reagent matrix material can be any material which can be effectively applied to impregnate the edges of the reagent matrix and provide water-repellency. Thus, materials such as oils, waxes, paraffin, silicones, printer's varnish can be utilized as well as polymeric materials. In addition to water-repellency, the sealing material should have the characteristic of reasonable viscosity at elevated temperatures such that it can be easily applied to the edges of reagent ribbon and then dry quickly at room temperature or a slightly elevated temperature and remain solid over the normal temperature range for reagent test devices. Clearly, there should be no interaction between the sealing material and the reagent(s) present in the reagent ribbon. Waxes are especially useful for this purpose since they are thermoplastic, water repellent, have a smooth texture, are nontoxic, and have freedom from any objectionable odor or color. Major types of waxes which can be employed include natural waxes, such as animal wax, beeswax, spermaceti, lanolin, shellac wax; vegetable waxes, such as carnauba, candelilla, bayberry, sugar cane; mineral waxes, such as fossil or earth waxes, including ozocerite, ceresin, montan; and petroleum waxes, such as paraffin, microcrystalline, petrolatum; as well as synthetic waxes such as ethylenic polymers and polyoleth-er-esters including Carbowax, sorbitol and cholorinated napthalenes such as Halowax and other hydrocarbon waxes.

The reagent ribbon or matrix material can be formed with any suitable material. U.S. Pat. No. 3,846,247 teaches the use of felt, porous ceramic material and woven or matted glass fibers. Additionally, U.S. Pat. No. 3,552,928 teaches the use of wood material, cloth, sponge material and argillaceous substances. The use of synthetic resin fleeces and glass fiber felts as carrier matrix is suggested in British Pat. No. 1,369,139. Another British Pat. No. 1,349,623, proposes the use of light permeable meshwork of thin filaments as a cover for an underlying paper matrix. Polyimide fibers are taught in French Pat. No. 2,170,397. Notwithstanding these suggestions, however, the material predominantly used in the art as a carrier matrix and that which is especially useful in the present invention is bibulous paper such as filter paper.

As indicated above, the reagent ribbon is normally impregnated and contains reagent material prior to the sealing of the edges of the reagent ribbon in accordance with the present invention. Following application of the sealing material to the edges of the reagent ribbon, and after any drying which may be required at room or elevated temperatures, the reagent ribbon can be fastened to a card of suitable substrate material such as Trycite (polystyrene) using double faced adhesive tape such as Doublestick available from the 3M Company. Following conventional techniques, the card containing reagent ribbons adhesively bound thereto is then cut widthwise to form reagent test devices. These reagent test devices can measure, for example, 8×0.5 centimeters having 0.5 centimeter squares of reagent laden carrier matrices at one end thereof, the other end serving as a handle for the reagent test device. Since the edges of the reagent matrix material which face each other on the resulting reagent test device are sealed by the sealing material in accordance with the present invention, liquid runover problem and the problems created by runover are effectively eliminated or substantially reduced.

From the foregoing, it will be seen that this invention is well adapted to attain all of the ends and objects hereinabove set forth, together with other advantages which are obvious and which are inherent to the system. The present invention have the advantages of convenience. simplicity, relatively inexpensiveness, positiveness, effectiveness, durability, accuracy and directness of action. The invention substantially overcomes problems associated with runover which have been a continuing and long felt problem with multiple reagent test devices. The invention provides a very effective, simple and inexpensive way of eliminating or materially reducing the runover problem. In addition, the present invention can effectively be utilized in conjunction with conventional techniques, or methods for forming reagent test devices. There is no extra layer which must be applied to reagent test devices in order to control the runover problem. Nevertheless, the present invention could be used in conjunction with other techniques found useful to control the runover problem if one so desired. Thus, the present invention could be utilized in conjunction with techniques in the prior art which rely on the use of hydrophobic barrier layers affixed to reagent test devices.

Obviously, many other modifications and variations of the invention as hereinbefore set forth can be made without departing from the spirit and scope and thereof.

What is claimed is:

1. A reagent test device comprising multiple reagent carrier matrices attached in spaced relationship to one side of a substrate, said reagent carrier matrices being impregnated with water repellent material on opposing facing edges in an amount sufficient to seal opposing facing edges to prevent liquid run-over between adjoining spaced carrier matrices.

2. The test device of claim 1 in which the carrier matrix is filter paper.

3. The test device of claim 1 in which the substrate is polystyrene.

4. The test device of claim 1 in which the water repellent material is paraffin.

5. The test device of claim 1 in which the water repellent material is an oil.

6. The test device of claim 1 in which the water repellent material is silicone.

7. A reagent test device comprising multiple reagent carrier matrices of filter paper attached in spaced relationship to one side of a polystyrene substrate, said reagent carrier matrices being impregnated with paraffin on opposing facing edges in an amount sufficient to seal on opposing facing edges of said matrices.

* * * * *